(12) United States Patent
Ruckstuhl et al.

(10) Patent No.: US 6,714,297 B1
(45) Date of Patent: Mar. 30, 2004

(54) LIGHT DETECTING OPTICAL DEVICE

(76) Inventors: Thomas Ruckstuhl, Hofweg 9, 8057 Zürich (CH); Stefan Seeger, Johann Wolfgang von Goethe Strasse 2, 93077 Michelstadt (DE)

(*) Notice: Subject to any disclaimer, the term of this patent is extended or adjusted under 35 U.S.C. 154(b) by 0 days.

(21) Appl. No.: 09/646,031
(22) PCT Filed: Mar. 10, 1999
(86) PCT No.: PCT/EP99/01548
§ 371 (c)(1),
(2), (4) Date: Jan. 11, 2001
(87) PCT Pub. No.: WO99/46596
PCT Pub. Date: Sep. 16, 1999

(30) Foreign Application Priority Data

Mar. 12, 1998 (DE) .......................... 198 10 615

(51) Int. Cl.[7] .......................... G01N 21/64; G01N 21/01
(52) U.S. Cl. ..................... 356/317; 356/318; 250/458.1
(58) Field of Search ............................... 356/317, 318, 356/417, 246; 250/458.1, 459.1, 461.1, 461.2

(56) References Cited

U.S. PATENT DOCUMENTS 5,721,435 A * 2/1998 Troll ...................... 250/559.29

FOREIGN PATENT DOCUMENTS

| DE | 30 15 054 A1 | 10/1981 |
| DE | 36 26 724 A1 | 2/1988 |
| DE | 42 26 884 C1 | 3/1994 |
| DE | 296 17 203 U1 | 1/1997 |
| DE | 196 28 002 C1 | 12/1997 |
| EP | 0 752 601 A1 | 9/1995 |

* cited by examiner

Primary Examiner—F. L. Evans
(74) Attorney, Agent, or Firm—Stephen E. Baldwin

(57) ABSTRACT

A fluorescing molecule is bound to an microscopic slide (24). The microscopic slide (24) is coupled to a first end face of an optical waveguide (1) by means of an immersion oil. The optical waveguide also possesses a shell surface (3) having the shape of a paraboloid of revolution, and a second end face (4). The molecule is located at the focal point of the paraboloid of revolution. Essentially the entire light of the molecule radiated into the half-space facing the optical waveguide (1) enters the optical waveguide (1). In particular, evanescent radiation (7) also enters the optical waveguide (1). This is totally internally reflected at the shell surface (3) having the shape of a paraboloid of revolution, emerges collimated from the second end face (4), and reaches a detector (30). In this way, essentially the entire evanescent radiation of the molecule can be registered. The optical arrangement thus improves the light-collecting efficiency for evanescent radiation, and thus the selective sensitivity of detection for molecules near the surface for fluorescence-based biosensors.

16 Claims, 3 Drawing Sheets

LIGHT DETECTING OPTICAL DEVICE

The invention relates to an optical arrangement for detecting light emitted by a sample.

The detection of molecules with the help of optical biosensors is done as a rule by detecting a specific binding between the molecules and what are called "receptor molecules", which are immobilized on a surface. The detection of molecules can be performed very selectively, even from a mixture, by way of such a specific binding. Antibodies or DNA molecules are typical receptor molecules. Typical surfaces are on optical fibers or transparent microscopic slides or cover sheets.

Often, a fluorescent signal specific to the binding between the molecule sought and the receptor molecule is detected in order to detect the molecules. This can be generated by the molecules sought themselves, if they are able to fluoresce.

However, as a rule, what is called a "sandwich test" is performed, in which the molecule sought is not able to fluoresce, but a third, fluorescence labeled "probe molecule" binds selectively to the binding complex of the molecule sought and the receptor molecule, after this complex has formed.

In order to obtain quantitative information on the quantity of the molecules sought bound to the receptor molecules, only that fluorescence light must be detected that indicates a binding complex between the molecule sought and the receptor molecule. Such a complex is always located close to that surface on which the receptor molecules are immobilized. From this, it follows that the measurement task is to detect selectively fluorescent signals from molecules bound close to the surface, that is, from near-surface layers.

Recently, the detection of near-surface fluorescence with the help of the detection of what is called "evanescent radiation" in optical sensors has proven effective. The following physical principle is exploited for this:

When a ray of light strikes an interface between a medium with a higher refractive index and one with a lower refractive index, total internal reflection can occur if the angle of incidence of the ray of light with respect to the surface normal is larger than the critical angle of total internal reflection ax, which is determined by $$\sin \alpha = \text{Error!} \quad (1)$$

(where $n_2$=index of refraction of the medium with a lower one, and $n_1$=index of refraction of the medium with a higher one). Rays of light that strike the interface at an angle larger than α cannot leave the medium with the higher refractive index, according to considerations of geometrical optics.

And vice-versa, it is not possible according to geometrical optics for a ray of light to penetrate from the medium with a lower index of refraction into the one with a higher index, if it propagates in the medium with the higher refractive index at an angle to the interface that is larger than the critical angle of total internal reflection α.

However, more precise electromagnetic considerations show that the field strength of the light wave striking the interface from the medium with the higher refractive index and being totally internally reflected does not drop abruptly to zero at the interface to the medium with the lower refractive index, but rather decreases exponentially from its value in the medium with the higher refractive index as a function of the distance from the interface. Typical decay constants for this exponential decline in the field strength lie in the range of the wavelength of the incident light. Thus despite total internal reflection, a certain portion of the light enters the medium with the lower refractive index.

Likewise, light from a location in the medium with the lower refractive index that is near the interface can also enter the medium with the higher refractive index at an angle that is greater than the critical angle of total internal reflection α.

This effect is exploited in optical fiber sensors. In these sensors, receptor molecules are immobilized on the surface of the fiber. Exciting light, usually laser light, is launched into the fiber. The laser light propagates along the fiber by total internal reflection. It also passes the regions of the fiber on whose surface the molecules able to fluoresce are bound. Due to the evanescent field of the exciting light at the surface of the fiber, molecules able to fluoresce can be excited. In the bound state, the distance of the molecules from the surface of the fiber is only a few nanometers, so that the exponential drop of the exciting light's field strength has little effect. Therefore, the molecules bound to the surface are effectively excited by the exciting light. The light emitted by the molecules can in turn be launched into the fiber, in part at angles at which the fluorescence light, once inside the fiber, propagates along the fiber due to total internal reflection. The propagated portion of fluorescence light from the bound molecules can then be detected at one end of the fiber.

A disadvantage of optical fiber sensors that detect evanescent radiation is that the efficiency with which they can collect (capture and transmit) emitted fluorescence photons is very limited. In particular, the sensitivity of such an arrangement is not sufficient to detect individual fluorescence molecules.

The object of the invention is to improve the light-collecting efficiency for light launched evanescently into a medium with a higher refractive index.

According to the present invention, this object is achieved by an optical arrangement.

The optical arrangement according to the invention can detect both light that has been generated on an interface, for example due to chemoluminescence, and also light scattered on the interface, for example fluorescence light due to excitation by a light source.

The light thus generated is collected by a light-collecting device. Besides the optical waveguide according to the invention, this can also include additional lenses, mirrors, filters, and other usual optical components.

The light collected by the light-collecting device is detected by the detection device. This also can include, in addition to an ordinary detector, additional lenses or filters for directing the light onto the detector.

The first end face may be entirely planar, or only flat in a region where the sample is located. The interface in front of which the sample is located can be formed directly by the first end face itself. Or alternatively, the first end face can be optically coupled to an interface between the sample medium and the medium with a high index of refraction. In this case, the medium with the high index of refraction can be the medium of an microscopic slide that is coupled to the first end face with the help of an immersion oil with a high refractive index. In the latter case, the diameter of the microscopic slide and the dimensions of the first end face should be selected so that light emitted by the sample, and radiated into the half-space facing the medium with a high index of refraction, is not prevented from entering the first end face by purely geometrical limitations.

If light is emitted by the sample near the interface, for example by generating fluorescence light, then a portion of the light enters the optical waveguide through the first end face, and propagates at an angle (with respect to the surface normal of the first end face at the site of the sample) within the optical waveguide which is larger than the critical angle of total internal reflection corresponding to the ratio of indices of refraction of the medium with a high index of refraction and the sample medium. In fiber sensors, this "evanescent" radiation could only propagate in part to the end of the fiber, and thus onto a detector. According to the invention, the arrangement and construction of the shell surface ensures that the evanescent radiation at the shell surface is totally reflected back into the optical waveguide. This can be done on the one hand by means of total internal reflection, or on the other hand by an appropriate mirror-coating of the shell surface. The evanescent radiation can then be directed onto a detection device and be detected by the latter according to prior art.

In this way, the evanescent portion of the radiation can be detected essentially entirely. Since also classical radiation can be detected, i.e. light that propagates in the optical waveguide at an angle (with respect to the surface normal mentioned above) that is smaller than the critical angle of total internal reflection corresponding to the ratio of indices of refraction of the medium with a high index of refraction and the sample medium, almost the entire radiation of a half-space can be detected.

In an advantageous embodiment, the first end face is flat. The shell surface adjacent to this is at such an angle to the first end face that the light emitted by the sample is totally reflected at the shell surface. In this way, no-loss reflection can be achieved. Further, a special mirror-coating of the shell surface is not needed.

In an advantageous embodiment of the invention, the arrangement and construction of the shell surface are selected so that essentially only the evanescent portion strikes the shell surface and is totally reflected at it. The classical radiation, on the other hand, leaves the optical waveguide unreflected.

This permits an extremely efficient separation of evanescent and classical radiation. Evanescent portions of radiation can only originate from sources close to the interface. Thus the light of a sample emitted near the surface can be detected very selectively, which is essential for optical biosensors.

In an advantageous embodiment of the invention, the optical waveguide is constructed to be symmetrical about an axis, and the sample is located on or in the immediate vicinity of the axis. The shell surface can then be a section of a paraboloid of revolution, with the sample being located near to the focal point. If the light emitted comes from the sample, and thus from the focal point of the paraboloid of revolution, it is collimated by reflection at the shell surface. Light thus collimated can be collected and detected in a simple way. If the second end face is flat, the collimated light will also emerge from the optical waveguide in parallel. It can then be handled especially easily. Furthermore, the radial distance of the ray of light emerging from the second end face depends in a well-defined way on the angle of entrance into the first end face.

In an advantageous embodiment of the invention, the shell surface is a section of an ellipsoid of revolution, with the sample being arranged near a focal point of the ellipsoid of revolution on or in front of the first end face.

This improvement is especially suitable for collecting and detecting classical and evanescent radiation in the second focal point of the ellipsoid of revolution beyond the second end face of the optical waveguide. In this way, a maximum efficiency of light collection can be achieved in an elegant fashion at sensor which is almost a point in size.

The shell surface can also be constructed as the outer surface of a frustum of a cone. This permits simple manufacturing of the optical waveguide. A frustum-shaped shell surface has also proven to provide an improved imaging quality, compared with a shell surface in the shape of a paraboloid of revolution, since deviations of the site of the radiation source from the axis have less effect on the sharpness of the image.

In another embodiment, the second end face is of convex construction, and acts as a focusing lens for the totally-reflected light. Thus the latter can be focused directly onto a point. The detection device can be located at this focal point, for example. This permits setting up the light-collecting device, which consists essentially of the optical waveguide.

In an advantageous embodiment of the invention, a light-absorbing aperture is arranged between the second end face and the detection device in such a way that it absorbs the classical radiation portion of the light emerging from the optical waveguide selectively. In most designs of the shell surface, the evanescent and classical portions of the radiation emerge at different places and/or at different angles from the second end face. An aperture is then able to absorb the classical radiation selectively from a mixture of classical and evanescent radiation, and only allow the evanescent radiation to pass. Selective detection of only the evanescent radiation in turn permits the selective detection of light emitted near the interface, which is important for optical biosensors.

Alternatively, the detection device can be constructed so that it detects classical and evanescent radiation separately. This can be done with the help of a detector with spatial resolution, for example. The separate detection of evanescent and classical radiation permits a further differentiation between light scattered near and far from the surface. The distance of the sample from the first interface can also be determined by this.

For detecting fluorescence light from a sample, the optical arrangement possesses a light source for irradiating the sample. The light can be transmitted through the optical waveguide onto the sample, for example by injecting it at the second end face, or injecting it in such a way that it excites the sample evanescently. As a rule, however, it is coupled into the waveguide at the sample end, and thus enters the optical waveguide through the first end face. In an advantageous improvement, an absorption device is located between the optical waveguide and the detection device, which absorbs the light from the light source so that it does not reach the detector. In this way, a disturbing influence of the light from the light source on the detection is prevented. This is essential for achieving the desired extremely high sensitivities, which permit detection of individual fluorescent molecules.

In an advantageous embodiment of the invention, a thin separating window made of a medium with a higher index of refraction is arranged between the first end face and the interface. Typically, this can be an microscopic slide or a microscopic cover sheet. The thickness of the separating window is substantially less than the minimum dimension of the first end face, so that the main portion of the evanescent radiation can enter the optical waveguide. This is particularly favorable for routine performance of analyses. Typically, receptor molecules are immobilized on a microscopic slide's surface in such cases. The microscopic slide is coupled optically to the first end face by an immersion oil on the opposite surface. In this way, direct contact between the optical waveguide and the sample, and thus contamination of the first end face, and resultant background signals, are avoided.

In an advantageous embodiment of the invention, the microscopic slide is mounted so that it can shift with respect to the optical waveguide in parallel to the first end face. The optical coupling between the optical waveguide and the microscopic slide remains even if the microscopic slide is shifted, due to the immersion oil. Thus it is possible to search the surface of a microscopic slide to see whether an individual or a few individual molecules sought have bound to the receptor molecules immobilized on it. This is important if extreme sensitivities are to be achieved, since the concentrations of the molecules sought are so small that no molecule sought may be bound to a receptor molecule in a predetermined small observation area.

In an advantageous embodiment of the invention, the microscopic slide is part of a flow cell. This permits automation of measurements and the analyzing of continuous flows of samples.

Advantageous embodiments of the invention are identified in the dependent claims.

In the following, the invention is explained in more detail by means of the embodiments shown in the drawing. In the drawing.

Figure 1:
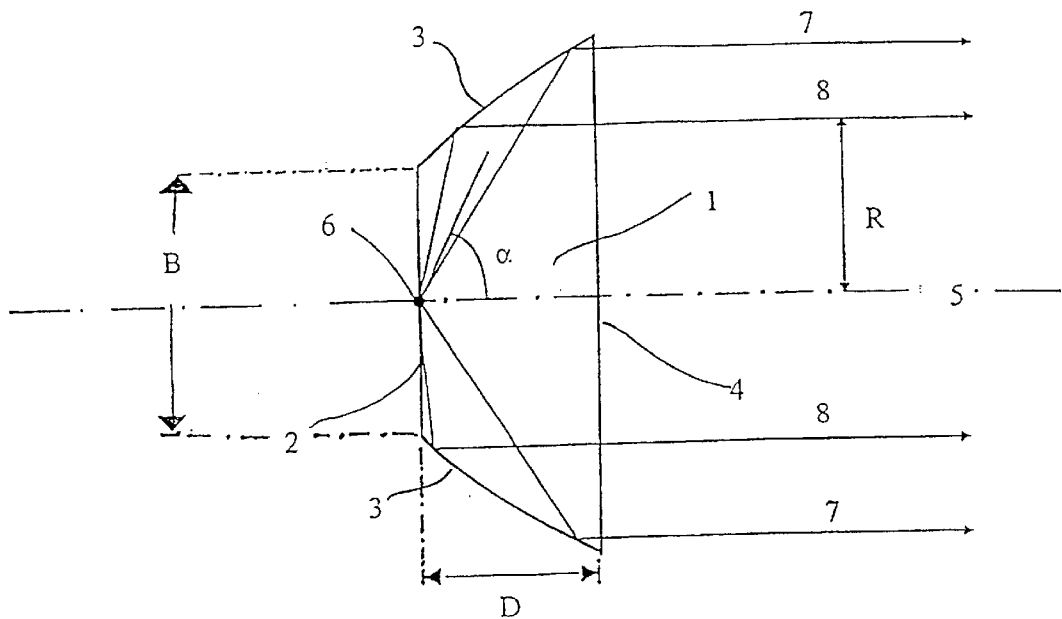
FIG. 1 shows a section through an optical waveguide according to the invention, with a shell surface having the shape of a paraboloid of revolution.

FIG. 1 shows an optical waveguide 1 with a flat first end face 2, shell surface 3 having the shape of a paraboloid of revolution, and a flat second end face 4. The optical waveguide is constructed to be symmetrical about an axis 5.

A typical material for the optical waveguide is glass with an index of refraction of 1.5. The sample is normally located in an aqueous solution with an index of refraction of about 1.3. However, other materials and media are also conceivable. For example, the optical waveguide could be surrounded by a liquid medium or another solid body (plastic/glass interface).

Light entering the optical waveguide 1 from a sample 6 comprises firstly the "classical" radiation 7. The classical radiation enters the optical waveguide 1 at an angle (with respect to the axis 5) that is smaller than the critical angle of total internal reflection corresponding to the ratio of indices of refraction of the optical waveguide material and the sample medium $\alpha$.

In addition, rays of light can enter the optical waveguide 1 at an angle that is larger than the critical angle of total internal reflection $\alpha$. These rays are called evanescent rays 8.

The distance R between the rays of light 7 and 8 reflected at the shell surface and the axis 5 only depends on the angle at which the respective ray of light leaving the sample 6 enters the optical waveguide 1. Therefore, the angle-of-radiation characteristics of the sample can be reconstructed from the radiation emerging through the second end face 4 with the help of a spatially resolving detector, for example a CCD camera.

By means of such a spatially resolving detector, the evanescent and the classical radiation can be detected simultaneously and can selectively be analyzed. This allows additional information to be obtained, e.g. on the distance of the sample from an interface.

The diameter B of the first end face can be selected freely. In case the sample and the focal point are in effect located on the first end face, the exact course of the parabola belonging to the paraboloid of revolution can be described by $$y = -\text{Error!} + \text{Error!} x^2, \quad (2)$$

where x is the distance of a point (x, y) on the parabola from the axis 5, and y is the distance of the point from the plane of the first end face.

Typical values for B lie in the range from 1 to 5 cm. However, miniaturized forms of the optical waveguide 1 with very small values for B, less than 100 $\mu$m, for example, are also conceivable.

The thickness D of the optical waveguide in the embodiment shown in FIG. 1 is selected so that both the evanescent radiation 8 and the classical radiation 7 are totally internally reflected at the shell surface 3 having the shape of a paraboloid of revolution.

In order to collect only the entire evanescent radiation from the sample, the dimensions of the optical waveguide 1 can be selected so that no classical radiation strikes the shell surface and is totally internally reflected. This can be achieved by selecting a correspondingly small thickness D of the optical waveguide 1. The minimum angle with respect to the axis of symmetry at which evanescent radiation propagates in the optical waveguide 1 is given by equation (1), taking into account the fact that $n_2$ is the index of refraction of the sample medium (typically water with an index of refraction of 1,3) and $n_1$ is the index of refraction of the optical waveguide (typically that of glass: 1.5). From this, an $\alpha$ of about 69° results. The intersection of a straight line running from the sample at an angle of 69° with respect to the axis 5 with the parabola y given above determines the thickness D of an optical waveguide that only reflects evanescent radiation.

Figure 2:
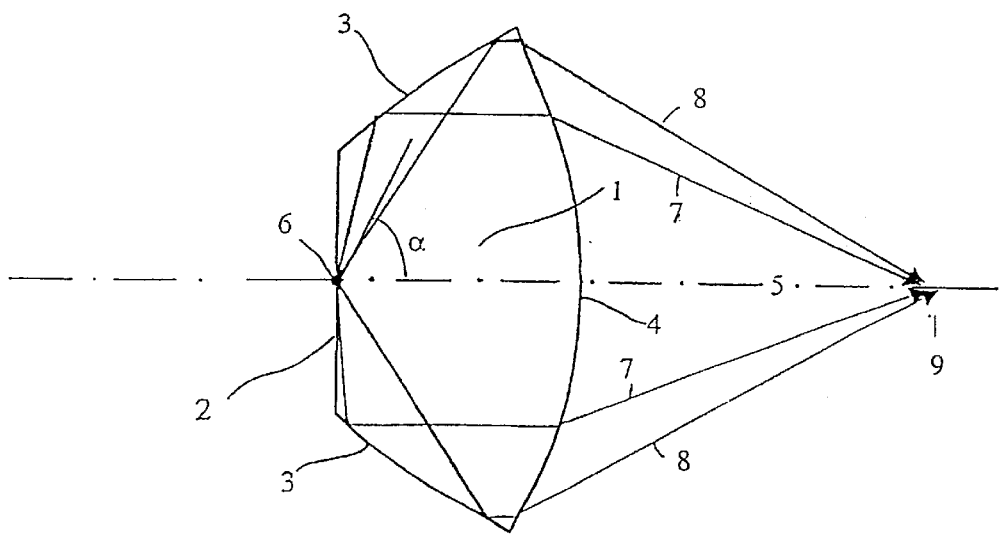
FIG. 2 shows the optical waveguide according to FIG. 1 with a convex second end face that acts as a focusing lens.

FIG. 2 shows the optical waveguide according to FIG. 1, but not with a flat second end face 4, but with a spherically convex second end face 4. Light entering the optical waveguide 1 from the sample 6 is collimated upon reflection from the shell surface 3 having the shape of a paraboloid of revolution, if the sample 6 is at the focal point of the paraboloid of revolution. The parallel rays of light 7 and 8 arising are focused onto a point 9 by the spherically convex second end face 4.

Figure 3:
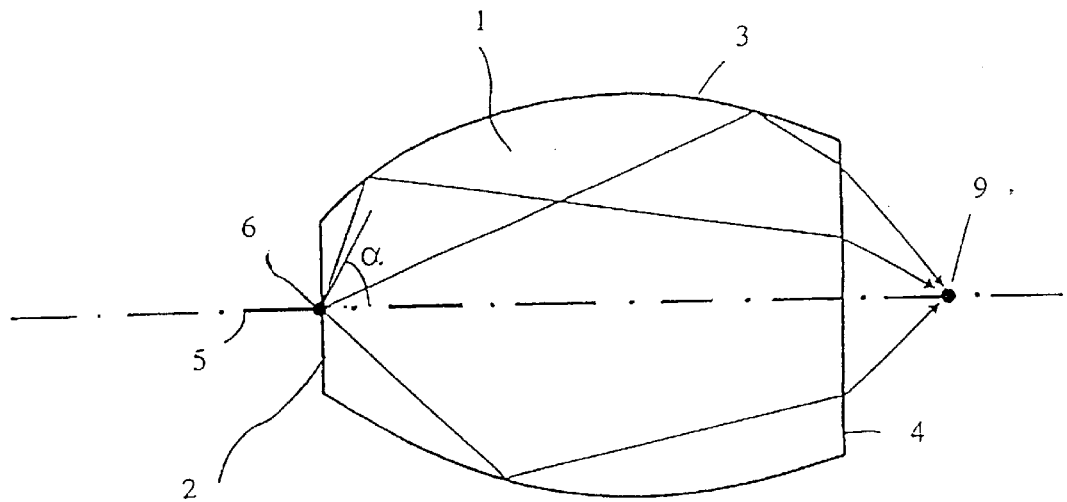
FIG. 3 shows a section through an optical waveguide according to the invention with a shell surface having the shape of an ellipsoid of revolution.

FIG. 3 shows an optical waveguide 1 with a flat first end face 2, a flat second end face 4, and a shell surface 3 having the shape of an ellipsoid of revolution. The sample 6 is located at one of the two focal points of the corresponding ellipsoid of revolution. Light emitted by the sample 6 that enters the optical waveguide 1 is mainly totally internally reflected at the shell surface 3 having the shape of an ellipsoid of revolution, and is focused at the second focal point of the ellipse. Since the second focal point lies outside the optical waveguide 1 in the embodiment shown here, the light is refracted towards the axis 5 when it emerges from the flat second end face 4. Therefore, the focus 9 lies somewhat closer to the optical waveguide 1 than the second focal point of the ellipsoid of revolution.

The second end face could just as well be spherically convex in design. The result of this would be that the focus 9 would lie even closer to the optical waveguide 1.

If the second end face 4 is spherically concave in design, with the midpoint of the corresponding sphere coinciding with the second focal point of the ellipse, then all rays reflected at the shell surface 3 having the shape of an ellipsoid of revolution emerge through the second end face 4 without being refracted, and the focus 9 and the second focal point of the ellipsoid of revolution coincide.

Figure 4:
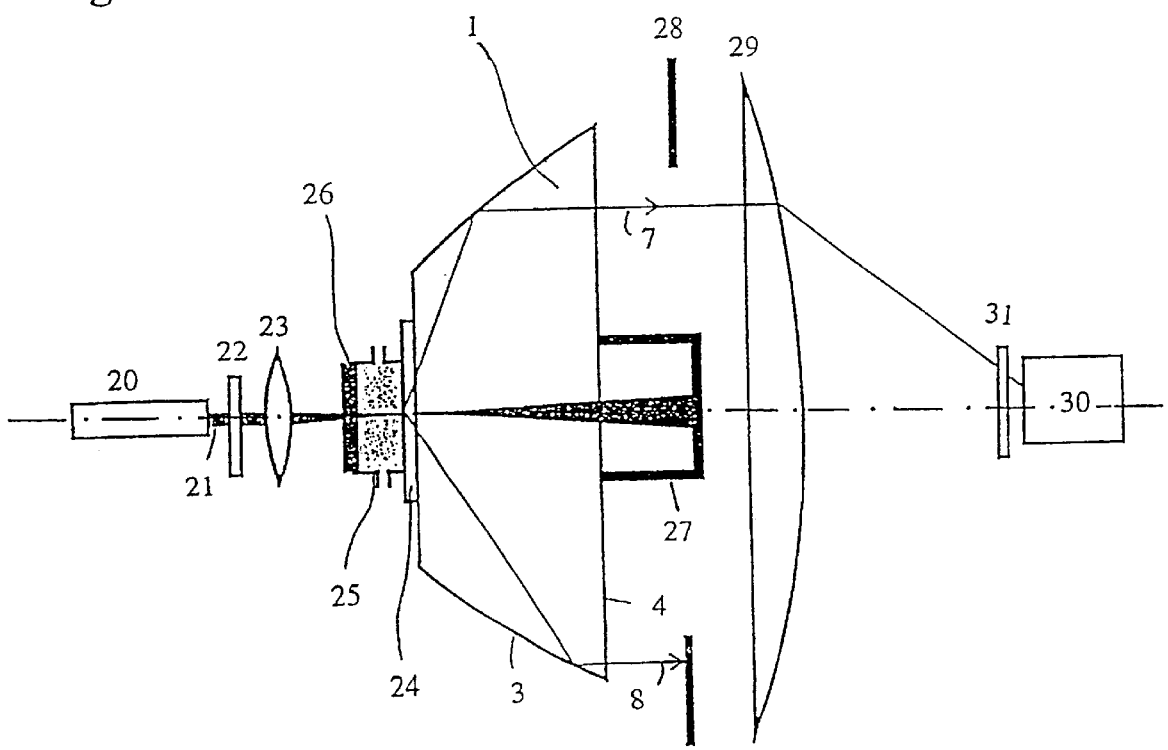
FIG. 4 shows a section through an optical arrangement according to the invention.

FIG. 4 shows an optical arrangement for detecting light emitted by a sample. A ray of light 21 emerges from a light source 20, which can be a diode laser, for example. This is first spectrally purified by an optical filter 22, since the radiation of diode lasers usually contains spectral components that do not coincide with the desired wavelength of the laser radiation. Next, the laser ray is focused onto the sample 6 by a focusing lens 23. An objective of a microscope can also serve as the focusing lens.

The sample 6 is located on the surface of an microscopic slide 24. The opposite surface of the microscopic slide is coupled optically to the optical waveguide 1 by an immersion oil. The microscopic slide 24 forms one wall of a flow cell 25. The wall 26 of the flow cell 25 that is opposite the microscopic slide 24 has a window that is transparent to the excitation wavelength.

On the microscopic slide 24, antibodies, for example, can be immobilized. A solution containing the molecules or antigens sought is now introduced into the flow cell. The medium in the sample cell can also be a gas within which the molecules sought are mixed, instead of a liquid.

The goal of the analysis is to determine the concentration of the antigens or their existence. For this purpose, the solution also contains second antibodies, known as "probe molecules", which bind selectively to the complex of the first antibody and the antigen bound to it. The first antibody is selective for the antigen, i.e. it forms a very specific binding, almost exclusively with the antigen. The probe molecule has a fluorescence label. The fluorescent dye must be selected so that its absorption wavelength coincides with the emission wavelength of the light source 20. If the light source is a diode laser with an emission wavelength of about 630 nm, for example, then a Rhodamine or Cyanine dye, such as Cy5, is a suitable dye. Typical antigens to be detected are tumor markers.

After passing through the sample 6, the microscopic slide 24, the immersion oil, and the optical waveguide 1, the laser ray 21 emerges from the optical waveguide 1 again through the second end face 4. It is captured there by an absorber 27.

The classical radiation 8 emitted by the sample 6 is absorbed by an annular aperture 28. The evanescent radiation 7 emitted by the sample reaches a focusing lens 29. Since the shell surface 3 has the shape of a paraboloid of revolution in this example, and is constructed so that the sample immobilized on the surface of the microscopic slide 24 is located at the focal point of the paraboloid of revolution, the evanescent radiation 7 leaves the optical waveguide 1 largely collimated.

The focusing lens 29, therefore, directs the evanescent radiation 7 onto the focal point of the focusing lens 29, where the detection device 30 is located.

This can be, for example, an avalanche photodiode suitable for counting single photons, a silicon PIN diode, a photomultiplier, or a CCD chip. In front of the detection device 30, there is another optical filter 31, usually an interference filter, which selectively passes only the fluorescence light of the dyes linked to the probe molecules. The interference filter blocks, in particular, light of the wavelength of light source 20 that has, for example, been scattered in the vicinity of sample 6.

Figure 5:
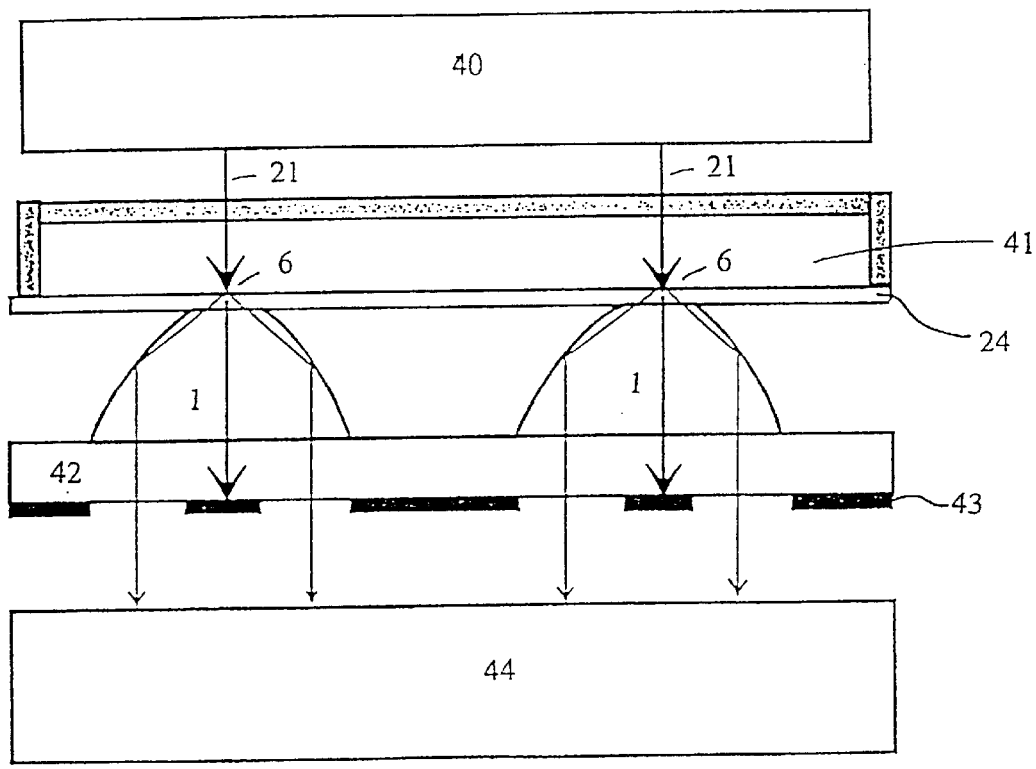
FIG. 5 shows a diagram of an embodiment of the optical arrangement according to the invention that is constructed from an array of individual optical arrangements.

FIG. 5 shows an embodiment of the optical arrangement in which a diagram of more than one excitation ray 21, more than one sample 6, and more than one light-collecting device, each with an optical waveguide 1, connected to more than one detection device, is shown. In the device 40 shown as a diagram, a plurality of light rays 21 is generated. This can occur either by a plurality of light sources, or by the division of one or a few light sources into a plurality of light rays, and subsequent focusing of these light rays, for example with an array of lenses or microlenses.

The light rays 21 enter a sample cell 41. The sample cell 41 is bounded on one side by a microscopic slide 24. On the microscopic slide, receptor molecules are immobilized in the usual way. The microscopic slide is coupled optically to a plurality of optical waveguides 1 by means of immersion oil. The latter are supported by a transparent holder 42. On the bottom of the transparent holder 42, an absorber mask 43 for absorbing the light rays 21 on the one hand, and the classical radiation on the other is arranged.

Below the transparent holder 42 there is a detection device 44, which can be the integrated circuit of a CCD camera, for example. By means of such a CCD camera, the course of the binding over time in the individual samples 6 can be tracked simultaneously.

Such an embodiment permits a parallelization arrangement of measuring points for a biosensor. Thus a speeding up of analyses can be achieved, on one hand. On the other hand, different receptor molecules can be immobilized on the surface of the microscopic slide 24 in the different samples, so that more than one analysis for differing molecules sought can be performed at the same time. Such a test is usually called a "multi-parameter test".

In the embodiment according to FIG. 5, a first array of lenses for generating numerous light rays 21 can be combined with a second array of lenses as part of the light-collecting device, with the dimensions of the two arrays being adjusted to the dimensions of the individual pixels of the integrated circuit of a CCD camera serving as a detection device.

Within the scope of the invention, numerous variations are possible. For example, the shape of shell surface 3 is not restricted to sections of a paraboloid or ellipsoid of revolution. A general paraboloid is also possible, such as one with an elliptical cross-section, which maps the light of the sample onto a line. The only important thing is that evanescent radiation be reflected as completely as possible at shell surface 3.

The first and second end faces can be arranged either in parallel or at an angle to one another.

The optical waveguide 1 can have, besides the three regions 2, 3 and 4 named, additional small regions in the transition regions between the areas.

As the light sources 20, all light sources normally used in spectroscopy can be used, i.e. in particular lamps and lasers of a wide variety of types.

What is claimed is:

1. Optical arrangement for detecting light emitted by a sample, having one or more optical waveguides which possess a first end face, a shell surface, and a second end face, with the sample being arranged in a sample medium in front of the first end face, and the one or more optical waveguide bodies consisting of a material that has a higher refractive index than the sample medium for the light emitted;

characterized in that
   the first end face is flat, at least in a region near the sample;
   the first end face forms an interface, or is optically coupled to an interface between the sample medium and a medium located in front of the first end face that has a higher refractive index than the sample medium, so that essentially the entire light emitted by the sample and radiated through the interface into a half-space facing the first end face, including evanescently radiated light, i.e. light radiated into the half-space above the angle of total internal reflection, enters the optical waveguide body through the first end face; and the shell surface and the second end face are arranged and constructed in such a way that essentially the entire evanescently radiated light radiated into the optical waveguide is totally internally reflected at the shell surface back into the optical waveguide, guided through the second end face, and directed onto a detection device.

2. Optical arrangement according to claim 1, characterized in that a thin separating window of the medium with a higher refractive index is arranged between the first end face and the interface, and the thickness of the separating window is considerably less than the minimum dimension of the first end face.

3. Optical arrangement according to claim 1, characterized in that the first end face is flat and the shell surface adjoining the first end face is at such an angle to the first end face that the light emitted by the sample strikes the shell surface at an angle to the respective surface normal which is larger than the critical angle of total internal reflection corresponding to the ratio of refractive indices of the optical waveguide material and of the ambient medium.

4. Optical arrangement according to claim 1, characterized in that the shell surface is constructed and arranged in such a way that essentially only the evanescently radiated portion of the light emitted by the sample and radiated into the optical waveguide strikes the shell surface.

5. Optical arrangement according to claim 1, characterized in that the optical waveguide is constructed to be symmetrical about an axis, with the sample being located on or in the immediate vicinity of the axis.

6. Optical arrangement according to claim 5, characterized in that the shell surface is a section of a paraboloid of revolution, with the sample being located near to the focal point in front of the first end face.

7. Optical arrangement according to claim 6, characterized in that the second end face is flat, and the light reflected from the shell surface emerges from the second end face in parallel rays.

8. Optical arrangement according to claim 5, characterized in that the shell surface is a section of an ellipsoid of revolution, with the sample being located near to a focal point of the ellipsoid of revolution in front of the first end face.

9. Optical arrangement according to claim 5, characterized in that the shell surface is constructed as a frustum of a cone.

10. Optical arrangement according to claim 9, characterized in that the second end face is of convex construction, and acts as a focusing lens for the totally internally reflected light.

11. Optical arrangement according to claim 5, characterized in that a light absorbing aperture is arranged between the second end face and the detection device in such a way that it absorbs that portion of the light emitted by the sample and propagated through the optical waveguide which enters the first end face at an angle to the surface normal that is smaller than the critical angle of total internal reflection corresponding to the ratio of refractive indices of the optical waveguide material and of the sample medium (classical radiation).

12. Optical arrangement according to claim 1, characterized in that it possesses a light source for irradiating the sample; and that the light source is arranged in such a way that its light is radiated onto the first end face from the sample side, and after passing through the optical waveguide is absorbed by an absorption device arranged between the optical waveguide and the detection device.

13. Optical arrangement according to claim 2, characterized in that the separating window is a microscopic slide that holds one or more samples on the surface facing away from the first end face.

14. Optical arrangement according to claim 13, characterized in that the microscopic slide is mounted in such a way that it can be shifted with respect to the optical waveguide in parallel to the first end face.

15. Optical arrangement according to claim 13, characterized in that the microscopic slide is part of a flow cell.

16. Optical arrangement according to claim 6, characterized in that the second end face is of convex construction, and acts as a focusing lens for the totally internally reflected light.

* * * * *